United States Patent
Voegele et al.

(10) Patent No.: US 6,241,687 B1
(45) Date of Patent: Jun. 5, 2001

(54) METHOD OF USE FOR A BIOPSY INSTRUMENT WITH BREAKABLE SAMPLE SEGMENTS

(75) Inventors: James Walden Voegele, Cincinnati, OH (US); David C. Brown, Chicago, IL (US); Paul Lawrence Erickson, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 09/506,916

(22) Filed: Feb. 18, 2000

(51) Int. Cl.[7] .................................................... A61B 10/00
(52) U.S. Cl. ........................................... 600/566; 606/185
(58) Field of Search .................................. 600/564, 566, 600/567; 606/184, 185

(56) References Cited

U.S. PATENT DOCUMENTS

| | | |
|---|---|---|
| 3,590,808 | 7/1971 | Muller . |
| 5,045,067 | 9/1991 | Ohnaka et al. . |
| 5,524,634 | 6/1996 | Turkel et al. . |
| 5,526,822 | 6/1996 | Burbank et al. . |

*Primary Examiner*—Robert L. Nasser
*Assistant Examiner*—Pamela L Wingood
(74) *Attorney, Agent, or Firm*—Louis J. Capezzuto

(57) ABSTRACT

A surgical biopsy instrument for the extraction of at least one tissue sample from a body is disclosed having a piercing needle for penetrating the body. The piercing needle has a piercing tip and a tissue receiving port. A cutting member having a distal sampling segment is used with the piercing needle. The sampling segment has a cutting edge and a bore therein. The sampling segment is breakable from the cutting member. A tissue sample is acquired within the sampling segment of the cutting member after the tissue sample is taken at the tissue receiving port of the piercing needle. The sampling segment is removed from the piercing needle and the sampling segment containing the tissue sample is removed from the cutting member.

9 Claims, 8 Drawing Sheets

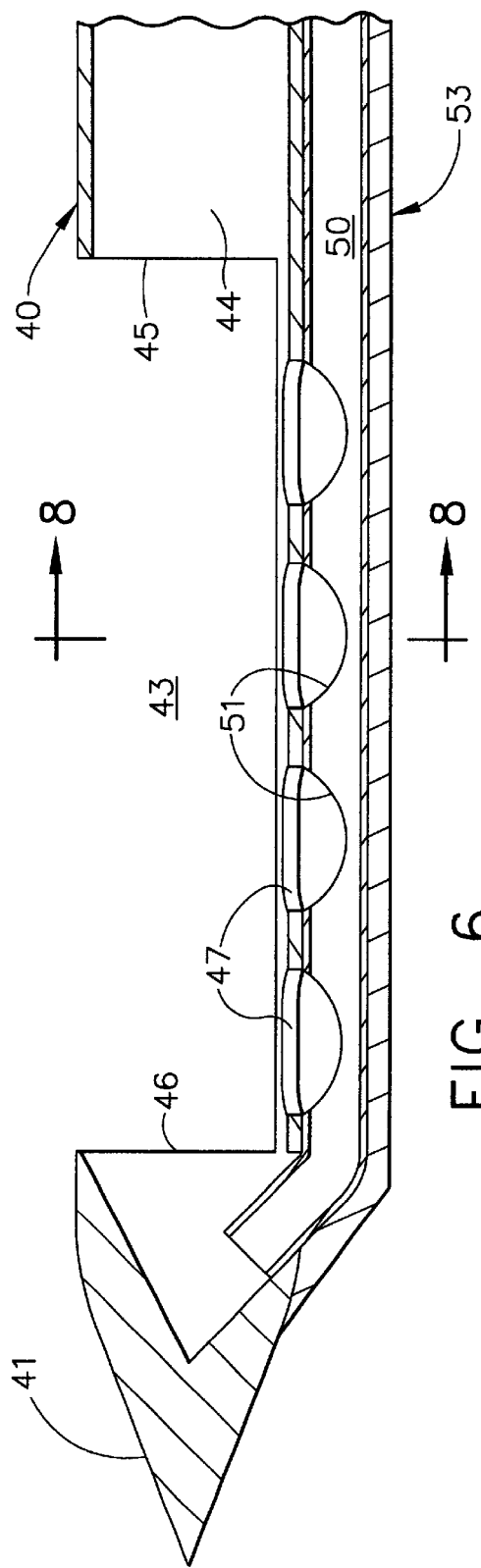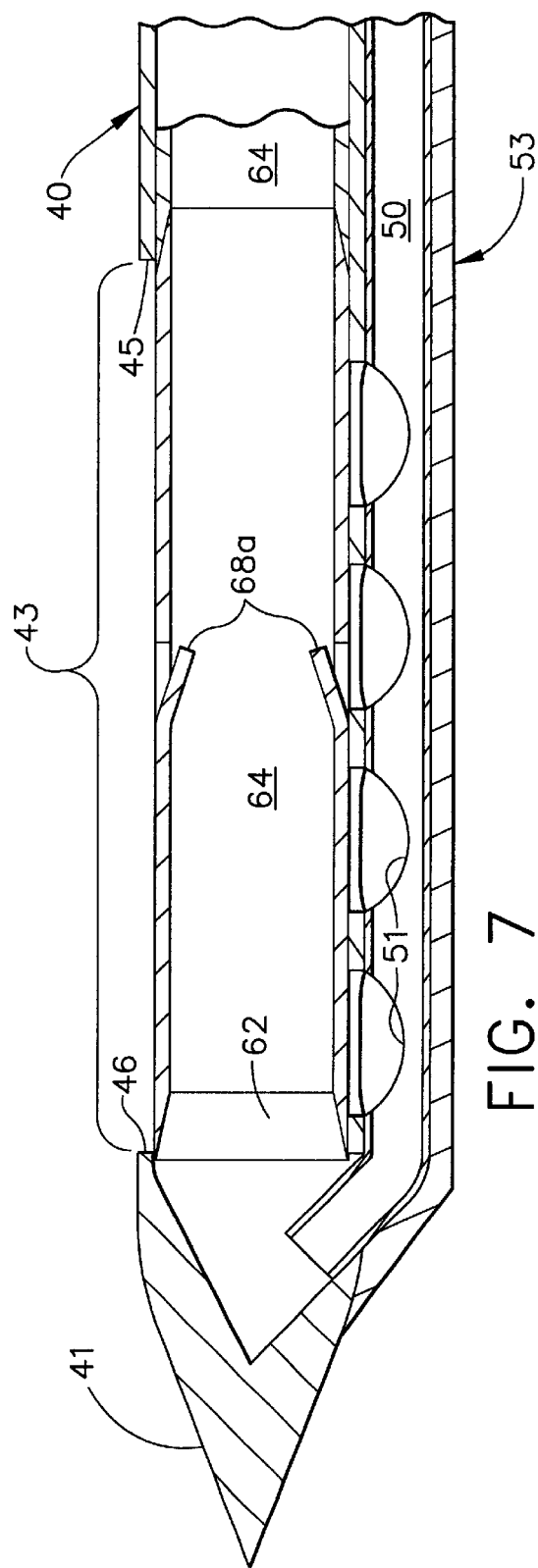

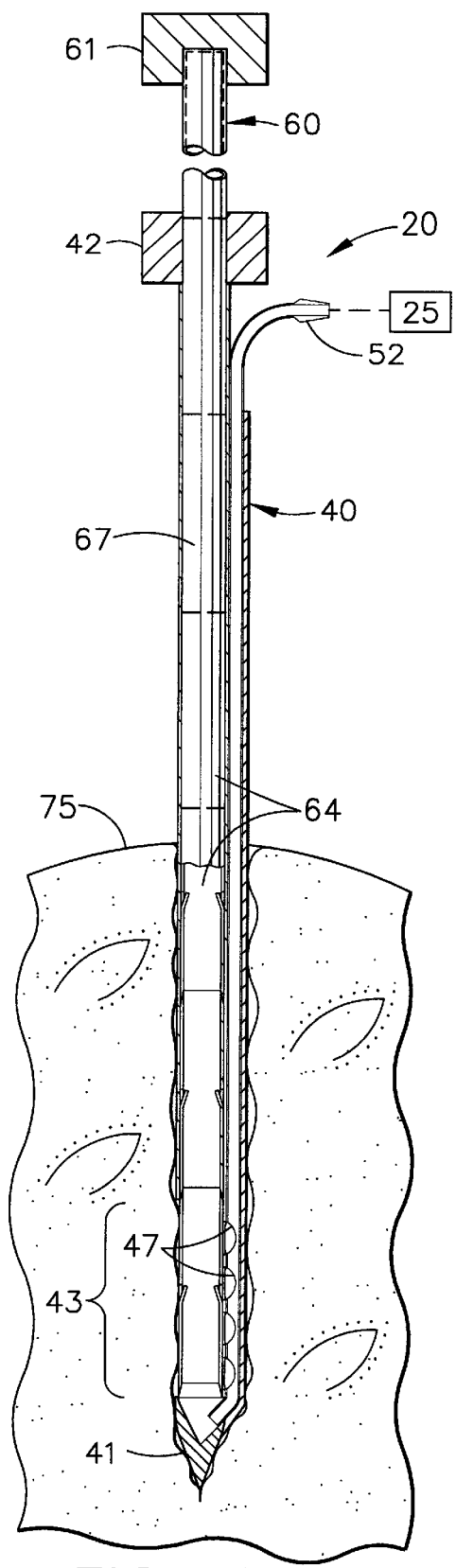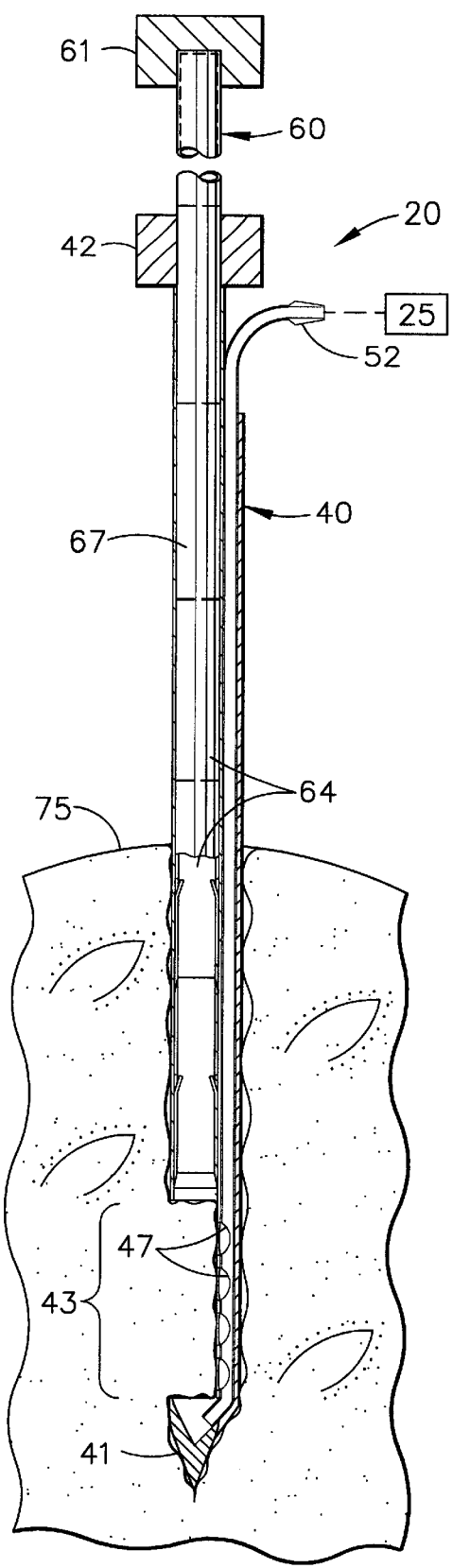
FIG. 10
FIG. 11

METHOD OF USE FOR A BIOPSY INSTRUMENT WITH BREAKABLE SAMPLE SEGMENTS

FIELD OF THE INVENTION

The present invention relates, in general, to biopsy instruments and methods of taking biopsies and, more particularly, to instruments and methods for acquiring multiple subcutaneous biopsies in a minimally invasive manner.

BACKGROUND OF THE INVENTION

Biopsies are performed on human patients in order to determine the nature of a suspicious growth, tumor or mass found on or inside the body. The growth can be initially identified by several methods, including visual examination, palpitation, x-ray, MRI, ultrasound imaging, or other detection means. Once identified, there is a pressing need to rapidly evaluate the tumor as to whether it is malignant (cancerous) or benign. A sample of suspect tissue is removed by biopsy, and then evaluated, generally under a microscope. If cancer is detected and treated in the early stages of growth, there is a significant increase in the survival rate of the patient.

While the need for an accurate biopsy sample of sufficient size to make a correct diagnosis is clear, scarring and disfigurement are also concerns, particularly when dealing with women's breast cancer. Recently, development efforts have focused on biopsy methods, which are less invasive than the current standard of care, the open excisional biopsy. Percutaneous methods for performing biopsies include fine needle aspiration (FNA) and core biopsies. Core biopsies are generally more accurate than FNA because they remove an intact sample of cells, simplifying diagnosis and post-biopsy relocation of suspected growths.

The original core biopsy devices consisted of a coring needle, i.e. a hollow tube with a sharpened edge, to obtain a plug of tissue. Such a device was inserted into the suspect region and withdrawn. Once the coring device was removed from the body, the plug of tissue was pushed out of the coring needle.

Although these coring needle devices provided a tissue core, they also removed a large section of healthy tissue in the process. They were also slow to use, and multiple puncture wounds were created in the breast when more than one sample was taken.

In response to the above deficiencies, an improved method of taking multiple biopsy samples was developed. The TRUE CUT® needle (sold by Travenol Laboratories, Deerfield, Ill.) provides the following advantages over the original core biopsy device or the use of hollow needles: 1) the TRUE CUT® device has a pointed stylus that enables the device to penetrate the body to the surgical site without removing a core of healthy tissue; 2) the device uses an exterior sliding cutter tube that covers or shields the biopsy or tissue sample within the device as it is being withdrawn. To obtain a tissue sample, the TRUE CUT® needle depends on the passive prolapse of tissue into a tissue receiving notch within the stylus. Once the tissue is prolapsed into the notch, the cutting tube is advanced to sever the tissue sample.

The above device was revolutionary in the field at the time because it removed tissue samples from the desired surgical site without affecting surrounding healthy tissue, and the instrument removed the sample from the body intact. However, the device still required multiple insertions and removals from the surgical site and subjected the tissue at the point of insertion to repeated tissue trauma. Additionally, its use was time consuming as the instrument required disassembly to remove each tissue sample. Moreover, the size and shape of the tissue samples tended to be inconsistent. This may have been caused by the need for the operator to wait for the tissue to passively prolapse into the device and by the forced migration of the tissue away from the cutter as it advanced.

In response to the need for a method to acquire consistent tissue samples, vacuum was added to biopsy instruments. The application of vacuum to the tissue receiving chamber of the biopsy instrument drew the tissue into the chamber. This type of device offered consistent tissue sample size and held the tissue in place as the knife was advanced to sever the tissue. U.S. Pat. No. 3,590,808 to Wulf Muller discloses such a device.

Whereas the Muller device did address the need for vacuum to effectively hold the tissue in place to provide consistent samples, it did require an insertion and removal of the device from the body for each tissue sample and accompanying tissue trauma.

Recognizing the shortcomings of the previous devices, an improved surgical biopsy device was developed and disclosed in U.S. Pat. No. 5,526,822 to Burbank et al. The device is embodied in the MAMMATOME® biopsy device. (manufactured and sold by Ethicon Endo-Surgery, Inc., Cincinnati, Ohio) It is an automated surgical biopsy device that is inserted into a surgical site and multiple tissue samples are removed from the instrument without withdrawing the instrument from the body. Additionally, vacuum is used to draw tissue into the instrument and to hold the tissue while it is cut. This provides the pathologist with elongated, intact tissue samples. This device includes an outer piercing needle with a single aperture port. A hollow tubular cutter having a single cutting edge is slidably and rotatably mounted within the outer piercing needle and cuts tissue drawn into the single aperture port. The cut tissue sample is captured within the hollow of the tubular cutter and is withdrawn from the surgical site within the tubular cutter. The tissue sample is then ejected from the tubular cutter into a biopsy cage or cartridge that holds multiple tissue samples for storage.

It is important to note that presently, the MAMMATOME® device utilizes a biopsy cage or cartridge that stores multiple tissue samples. Placement of the samples into the cage can be time consuming and care must be taken to place the samples in some sequence of order to ensure proper analysis by pathology.

One type of known sample handling mechanism and technique is disclosed in U.S. Pat. No. 5,524,634 (Turkel et al.). However, Turkel et al. only teaches a particular container and method of storing and labeling tissue samples.

Presently, there is no known surgical biopsy device and its method of use that can meet all of the needs outlined above in addition to providing an efficient mechanism for protection and identification of multiple biopsy samples.

SUMMARY OF THE INVENTION

Accordingly, the present invention is a method for extracting at least one tissue sample from a body. The method comprises initially inserting a surgical biopsy instrument into the body. The surgical biopsy instrument has a piercing needle having a piercing tip and a tissue receiving port. A cutting member is provided, the cutting member having a distal sampling segment. The sampling segment has a cutting edge and a bore therein and the sampling segment is breakable from the cutting member.

A tissue sample is acquired within the sampling segment of the cutting member. The tissue sample is taken at the tissue receiving port of the piercing needle and the sampling segment containing the tissue sample is removed from the piercing needle. The sampling segment containing the tissue sample is broken from the cutting member.

Significantly, the novel method of use of the novel surgical biopsy instrument for extracting at least one tissue sample from a body enhances the surgeon's capabilities during an operative procedure. Specifically, the breakable distal sampling segments of the cutting member enables the surgeon to acquire multiple subcutaneous biopsies, each of which is retained in a separate sampling segment. This is especially significant, as the retention of each sample in a separate sampling segment protects the tissue samples from contact contamination with other tissue samples. Also, the tissue receiving port of the piercing needle is sized shorter than the sampling segment so that when a tissue sample is taken, the tissue sample is shorter than the sampling segment to reduce possible contact contamination with other tissue.

Additionally, the use of separate sampling segments provides an opportunity to uniquely label or identify each tissue sample from all others. This is accomplished by placing a unique identifier on each of the sampling segments. That is, the addition of a unique number, letter, or a bar code to each sampling segment uniquely identifies each tissue sample. This is especially significant as the location of each tissue sample taken from the patient can be logged, and the sample checked to determine if all unwanted tissue was removed from the patient. If additional surgery is required, the location of the unwanted tissue can easily be determined from the log.

Additionally, the breakable sampling segments provide the surgeon with a fresh cutting edge for each tissue sample obtained. The fresh cutting edge ensures that each tissue sample will be cut in a clean and consistent manner, and that a dull blade will not smear the tissue samples. Consequently, the surgeon is provided with improved tissue samples and improved analysis of the tissue samples.

For a better understanding of the invention and its unique features, reference is made to the accompanying drawings and descriptive matter in which the preferred invention is fully described.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 6 is an enlarged cross-sectional side view of the distal end of the surgical biopsy instrument of FIG. 5 with the cutting member retracted out of the view;

FIG. 7 is an enlarged cross-sectional side view of the distal end of the surgical biopsy instrument of FIG. 6 with the cutting member moved to the fully inserted position;

FIG. 10 is a cross-sectional side view of the surgical biopsy instrument of FIG. 9 with the surgical biopsy instrument inserted into the breast of a patient;

FIG. 11 is a cross-sectional side view of the surgical biopsy instrument of FIG. 10 with the cutting member retracted and the vacuum source actuated to draw tissue into a tissue receiving port of the surgical biopsy instrument;

DETAILED DESCRIPTION OF THE INVENTION

Figure 1:
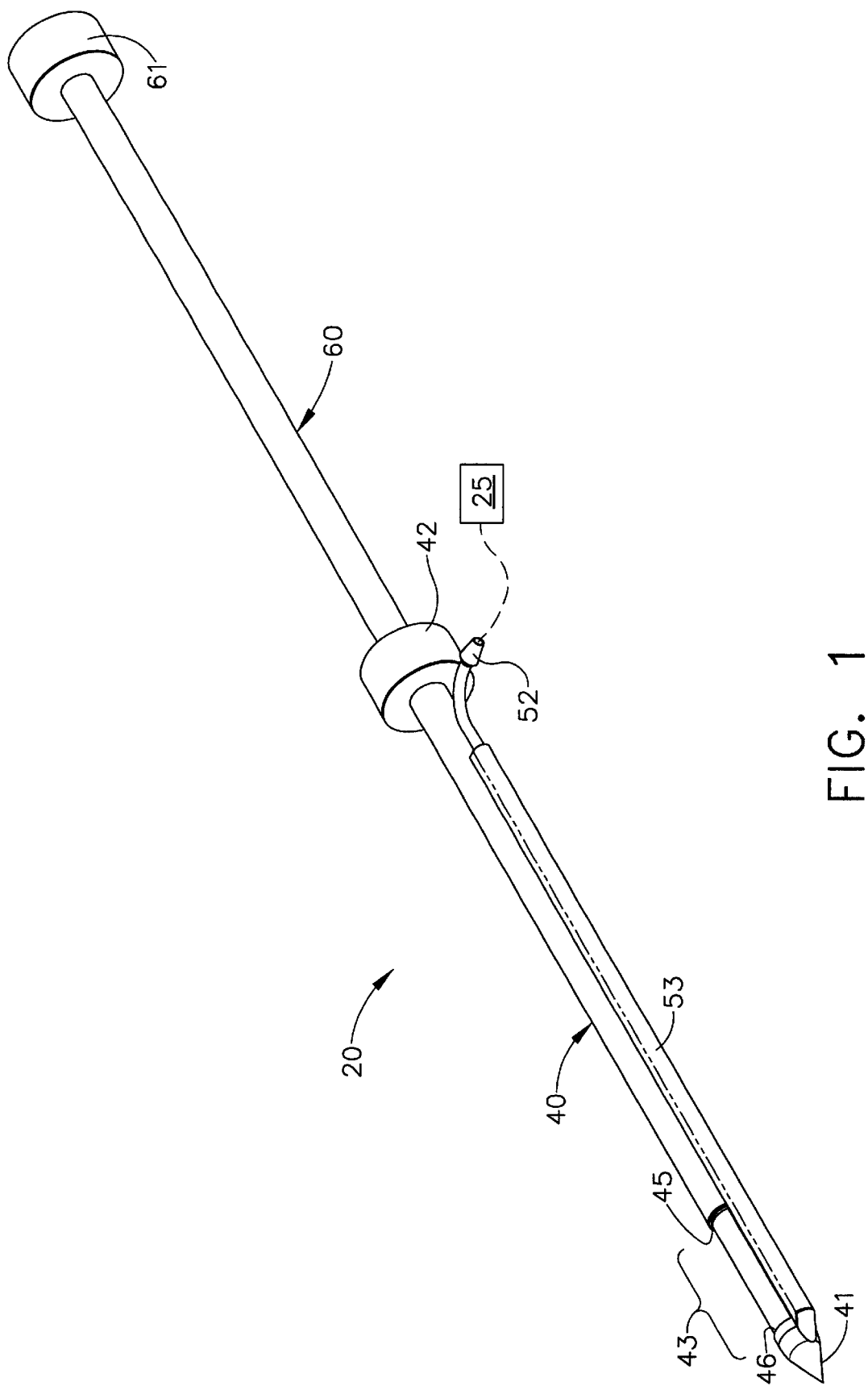
FIG. 1 is an isometric view of a surgical biopsy instrument of the present invention operably coupled to a vacuum source.

The present invention relates, in general, to surgical biopsy instruments and methods of acquiring multiple subcutaneous tissue biopsies in a minimally invasive manner. In particular, the present invention is an improved surgical instrument that provides multiple cutting edges to ensure blade sharpness and provides a novel method of tissue sample storage and identification. As best shown in FIG. 1, the present invention is a surgical biopsy instrument 20 which has a piercing needle 40 for the penetration of tissue, such as breast tissue, and a cutting member 60 moveable within a passageway 44 (FIG. 2) of the piercing needle 40 for the cutting and removal of a plurality of tissue samples 30 (FIG. 12) therefrom. A vacuum source 25 is shown operably coupled to the hollow piercing needle 40 to draw tissue samples into the surgical biopsy instrument 20.

Figure 2:
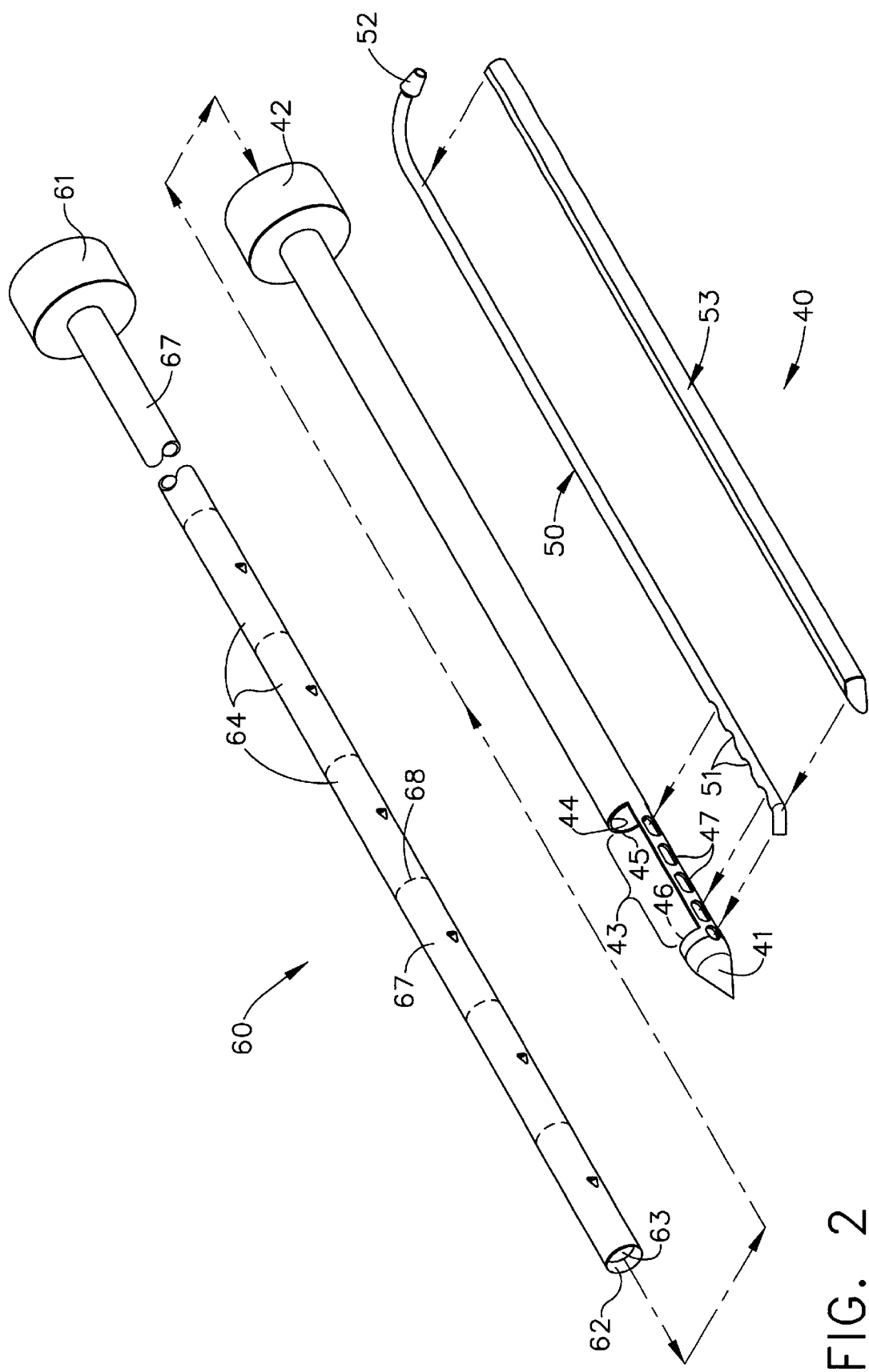
FIG. 2 is an exploded isometric view of the piercing needle of the surgical biopsy instrument of FIG. 1 and an assembled view of a cutting member of the surgical biopsy instrument.

As illustrated in FIGS. 1 and 2, the piercing needle 40 has a distal piercing tip 41 for piercing tissue and a proximal knob 42 for the operator to hold. A tissue receiving port 43 is located adjacent to the piercing tip 41 for the reception of tissue samples therein. The tissue receiving port 43 communicates with the passageway 44—extending from the piercing tip 41 and open at a proximal end of the knob 42 (FIG. 5) for the reception of the cutting member 60. Tissue receiving port 43 also has a proximal port edge 45 and a distal port edge 46.

A plurality of manifold ports 47 are located within the base of the tissue receiving port 43 and are operably coupled to a vacuum line 50 extending along the exterior of the piercing needle 40. Notches 51 are located within the vacuum line 50 to couple the vacuum line 50 to the manifold ports 47 of the piercing needle 40. A vacuum connector 52 is provided at the distal end of the vacuum line 50. The vacuum source is operatively coupled to the piercing needle 40 at the vacuum connector 52. The vacuum line 50 and a line cover 53 are fixedly attached to the piercing needle 40 by solder, glue, braze or any other airtight attachment means.

Cutting member 60 is slidably and removably received within the passageway 44 of the piercing needle 40, and has a proximal grip 61 for the operator to grasp and a distal cutting edge 62 for the cutting of tissue samples. Cutting member 60 is hollow and has a bore 63 extending distally from the grip 61 to the cutting edge 62 for the reception of cut tissue samples therein. The cutting member 60 of the preferred invention is rigid and is assembled from a plurality of sampling segments 64 and a shaft 67.

Figure 4:
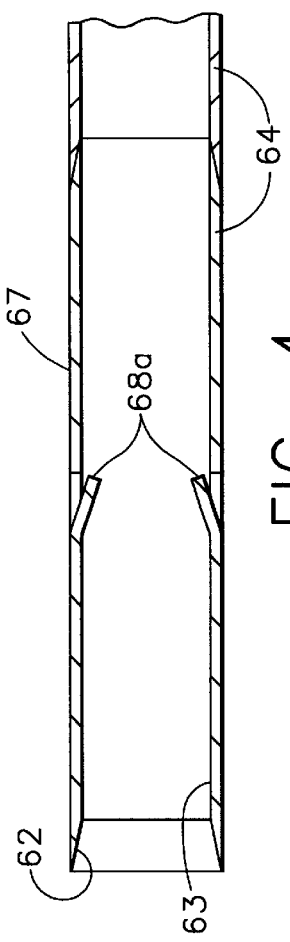
FIG. 4 is a fragmentary cross-sectional side view of the distal end of the assembled cutting member of FIG. 2 showing the assembly of the individual sample segments.
Figure 3:
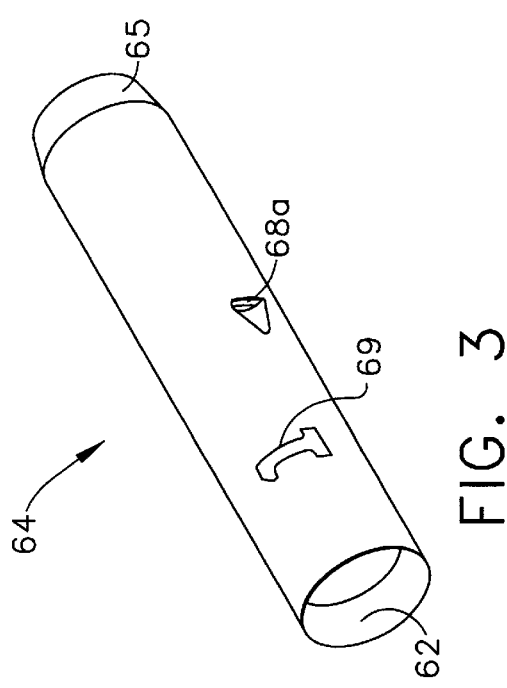
FIG. 3 is an isometric view of a single sample segment of the cutting member of the surgical biopsy instrument shown in FIG. 2, the sample segment for the reception of a tissue sample therein.

Turning now to FIGS. 3 and 4, the sampling segments 64 are formed as separate discreet members, for instance cylinders. Each sampling segment has a proximal tapered end 65 and the distal cutting edge 62. The longitudinal length of the sampling segments 64 is slightly longer than the longitudinal length of the tissue receiving port 43 of the piercing needle 40 (FIG. 5) and this will be explained in greater detail below. As best shown in FIG. 4, the angle of the distal tapered end 65 and the distal cutting edge 62 are generally the same so that the sampling segments 64 can nest together to form a stack of sampling segments 64. It is an object of the preferred invention to frangibly or breakably assemble the sampling segments 64 together with the proximal shaft 67 to form the cutting member 60 (FIG. 2). The frangible assembly of the cutting member 60 provides the operator with a cutting member 60 that is rigid enough to cut a tissue sample, yet frangible so that the operator can break off the distal-most sampling segment 64 once the tissue sample is taken. By breaking off the sampling segment 64 of the present invention, the operator is guaranteed a new and ready cutting edge 62 for each tissue sample taken such that each tissue sample is held within its own sampling segment 64 for analysis later.

The sampling segments 64 of the preferred invention are preferably held together by an external frangible layer 67 formed from a portion of medical grade shrink tubing. A plurality of perforations 68 are placed within the shrink tubing of the external frangible layer 67 at the junction of two sampling segments 64 to reduce the force to break the frangible layer 67. Whereas the preferred embodiment is a shrink tubing, the sampling segments 64 can be breakably attached in a variety of ways including but not limited to: a thin plating, a coating of paint, adhesives, molded plastics, or any one of a number of other frangible attachment methods. These frangible attachment methods can be used in combination with perforations 68.

The sampling segments 64 have at least one sample retainer 68a extending into the bore 63 for the retention of tissue samples therein. As shown in FIG. 4, the sample retainers 68a are angled inwardly and provide a ramped surface as tissue enters the sampling segment 64. The sample retainers 68a effectively act as a one way tissue passage feature within the sampling segments 64 and resist the extraction of the tissue sample in the opposite direction.

An identifier (indicia) 69 (FIG. 3) is located on the exterior of each sampling segment 64 to provide identification so that each sample can be properly accounted for. This enables the surgical team to uniquely identify and record (or log) the identifier 69 of each sampling segment 64 along with the site from which the tissue sample was taken. This reduces the possibility of mixing unmarked tissue samples. The identifiers 69 are most preferably sequential numbers, with a different number on each sampling segment. Whereas numbers are the preferred embodiment, letters, symbols, colors, bar codes, or any other identification system can be used.

Figure 5:
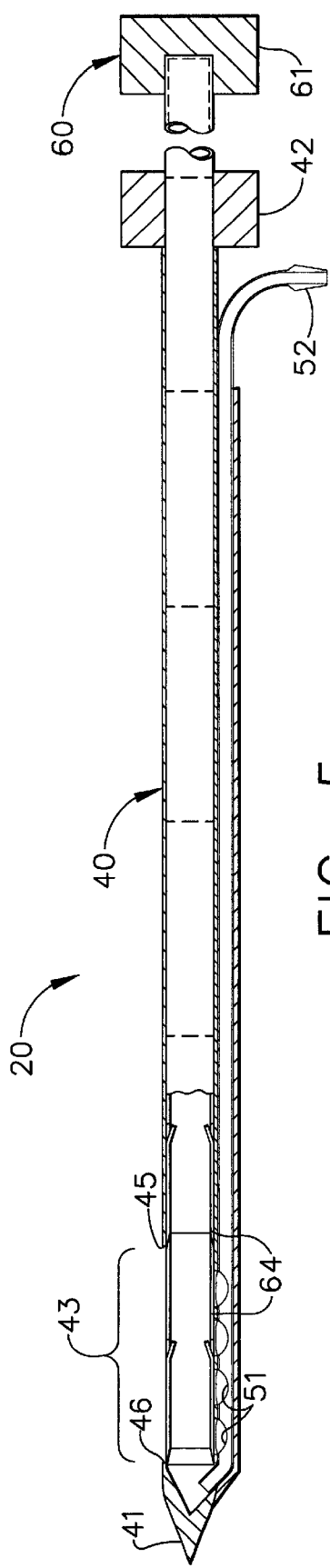
FIG. 5 is a cross-sectional side view of the surgical biopsy instrument of FIG. 1.
Figure 8:
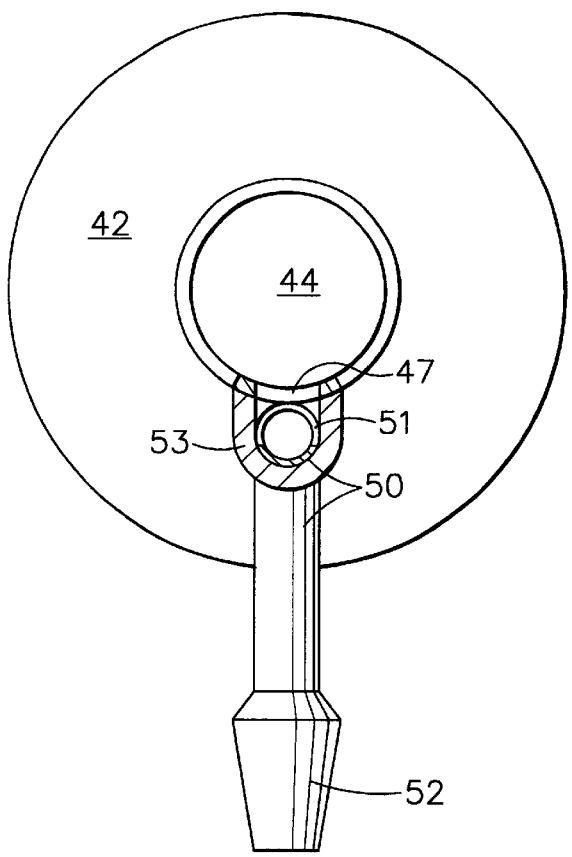
FIG. 8 is a cross sectional view of the distal end of the surgical biopsy instrument of FIG. 6, with the cross section taken perpendicular to the longitudinal axis of the surgical biopsy instrument.
Figure 12:
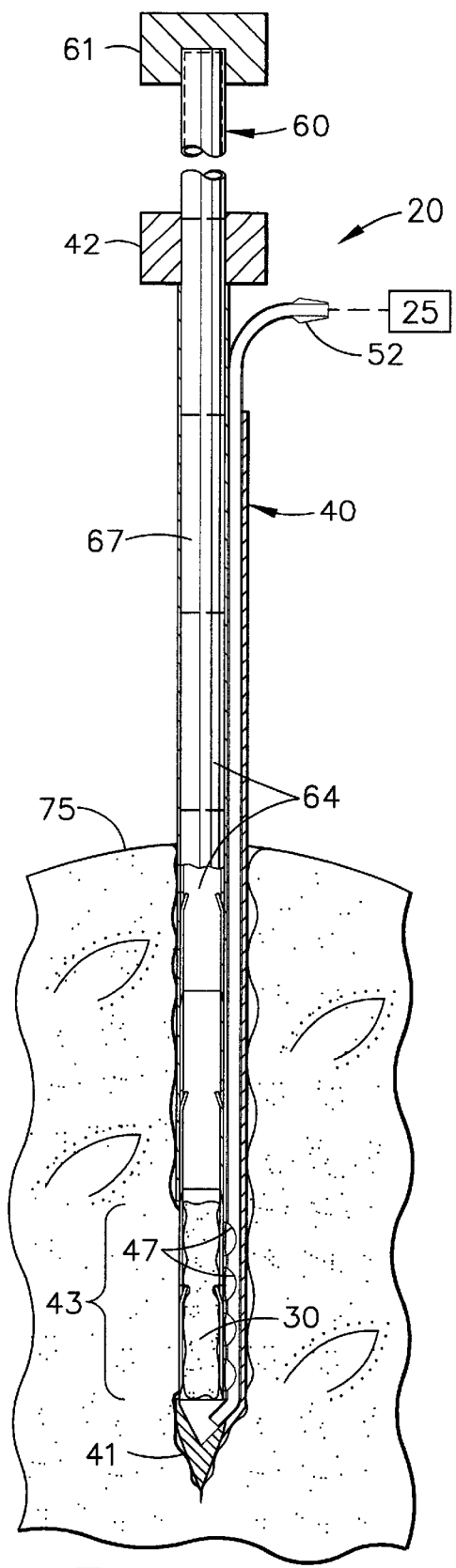
FIG. 12 is a cross-sectional side view of the surgical biopsy instrument of FIG. 11 with the cutting member extended to sever a tissue sample therein.

FIGS. 5–8 are cross-sections of the surgical biopsy instrument 20. FIG. 5 shows a cross section of the assembled surgical biopsy instrument 20 with the cutting member 60 fully inserted into the piercing needle 40. FIGS. 6–7 are of the distal end of the proximal end of the surgical biopsy instrument 20 and show the movement of the cutting edge 62 relative to the tissue receiving port 43. In FIG. 7, the cutting member 60 is shown fully inserted into the piercing needle 40 to show how the cutting edge 62 of the sampling segment 64 has traveled past the distal port edge 46 of the tissue receiving port 43. This final portion of the travel ensures complete severance of a tissue sample 30 (FIG. 12). FIG. 6 also shows that the sampling segment 64 is longer than the tissue receiving port 43. A cross section of the piercing needle 40 is shown in FIG. 8, with the cross section taken across the notches 51 of the tubular vacuum line 50 and the manifold ports 47 of the piercing needle 40.

Figure 9:
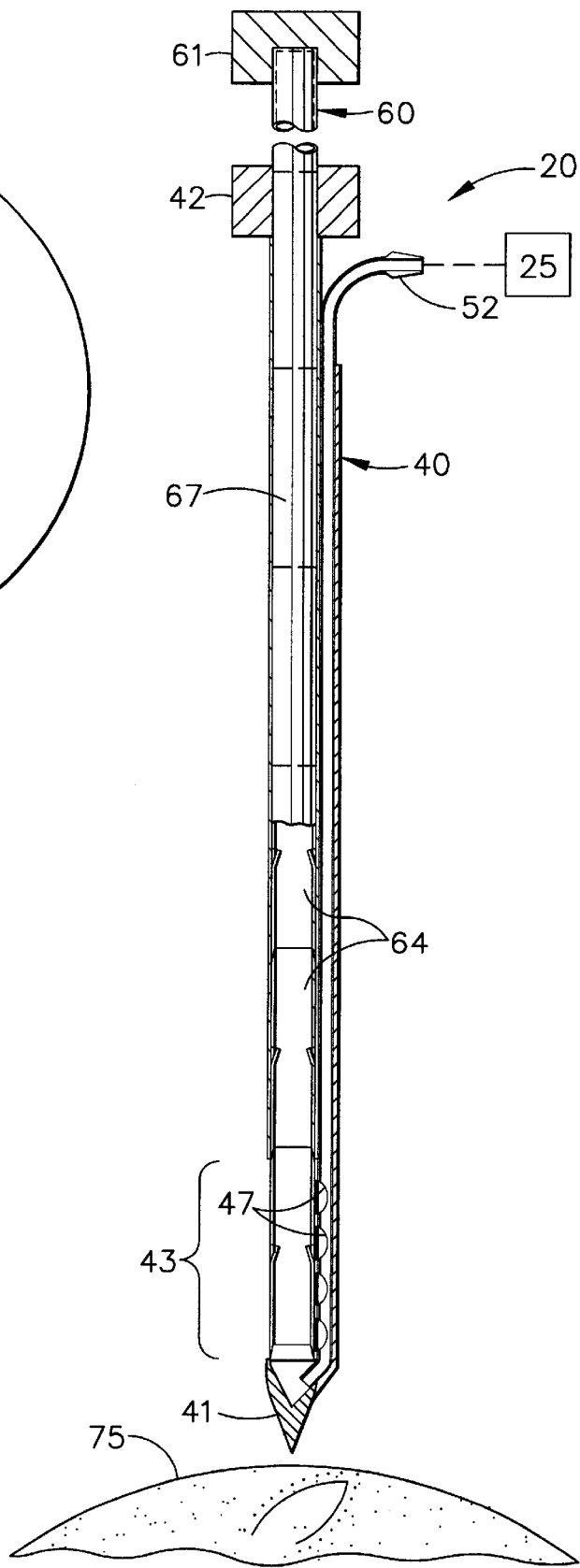
FIG. 9 is a cross-sectional side view of the surgical biopsy instrument of FIG. 5 poised above a breast of a patient.

FIGS. 9–14 best illustrate the method of use according to the present invention. The surgical biopsy device 20 (FIG. 1) is used to obtain multiple biopsy samples from a surgical site within a patient's tissue, such as breast 75. The patient is generally positioned upon a surgical table (not shown) and is given a local anesthetic to anesthetize the desired penetration site. In FIG. 9, the preferred surgical biopsy instrument 20 is shown poised above the breast 75 of the patient just prior to penetration for the taking of multiple tissue samples 30 therefrom. Although the breast 75 is depicted, it should be obvious that tissue samples can be acquired from any number of surgical sites or organs within the body, and the preferred surgical biopsy instrument 20 is not limited to breast use. The piercing tip 41 is shown placed just above the breast 75 and will facilitate the passage of the surgical biopsy 20 into the breast. The cutting member 60 is fully extended into the piercing needle 40 to close the tissue receiving port 43 so that tissue cannot migrate therein until desired.

Next, as shown in FIG. 10, the surgical biopsy instrument 20 is placed into the breast 75 by the surgeon. As shown in FIG. 11, the surgical biopsy instrument 20 is carefully positioned at the suspect tissue region and the cutting member 60 is retracted to open the tissue receiving port 43. The vacuum source 25 is activated to draw tissue into the tissue receiving port 43 and against the manifold ports 47. The tissue is held in this position prior to the cutting of the tissue sample. The manifold ports 47 are placed within the tissue receiving port to draw tissue into the receiving port 43 and not into the passageway 64. This limits the length of the tissue sample that will be acquired.

In FIG. 12, the cutting member 60 has been advanced downward to sever the tissue sample 30 from the breast 75. The tissue sample 30 resides within the bore 63 of the distal-most sampling segment 64 and does not extend the proximal and distal end of the sampling segment 64. By confining the tissue sample 30 within the sampling segment 64, the potential for contaminating the tissue sample 30 with cells from another tissue sample 30 (not shown) is reduced. The tissue retainers 66 retain the tissue sample 30 within the sampling segment 64. In FIG. 12, the vacuum from the vacuum source 25 has been turned off and the tissue sample 30 is ready for removal from the patient.

Figure 13:
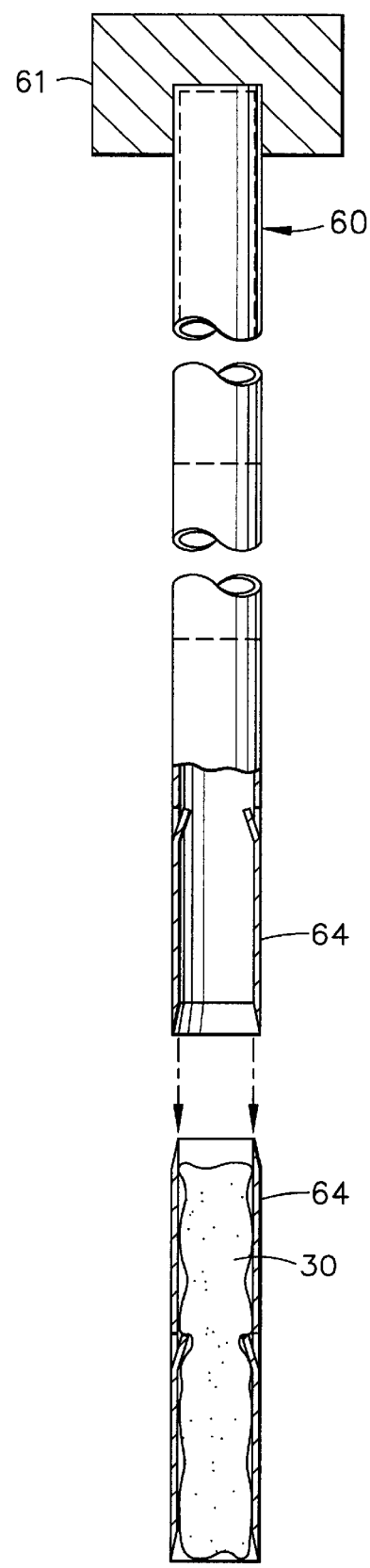
FIG. 13 is a cross-sectional side view of the cutting member of the surgical biopsy instrument with the distal-most sample segment and containing the tissue sample broken off of the cutting member.

FIG. 13 shows the cutting member 60 after removal from the piercing needle 40 and from the patient. The distal-most sampling segment 64 has been broken and detached from the cutting member 60 and contains the tissue sample 30 therein. Once the sample is detached, it is placed into a container for delivery to a laboratory such as the pathology department for analysis. The sampling segment 64, numbered with its identifier (not shown) identifies the sequence of the tissue sample 30. Accordingly, new cutting edge 62 is exposed at the distal end of the cutting member 60 whenever a sampling segment 64 and sample 30 are detached.

Figure 14:
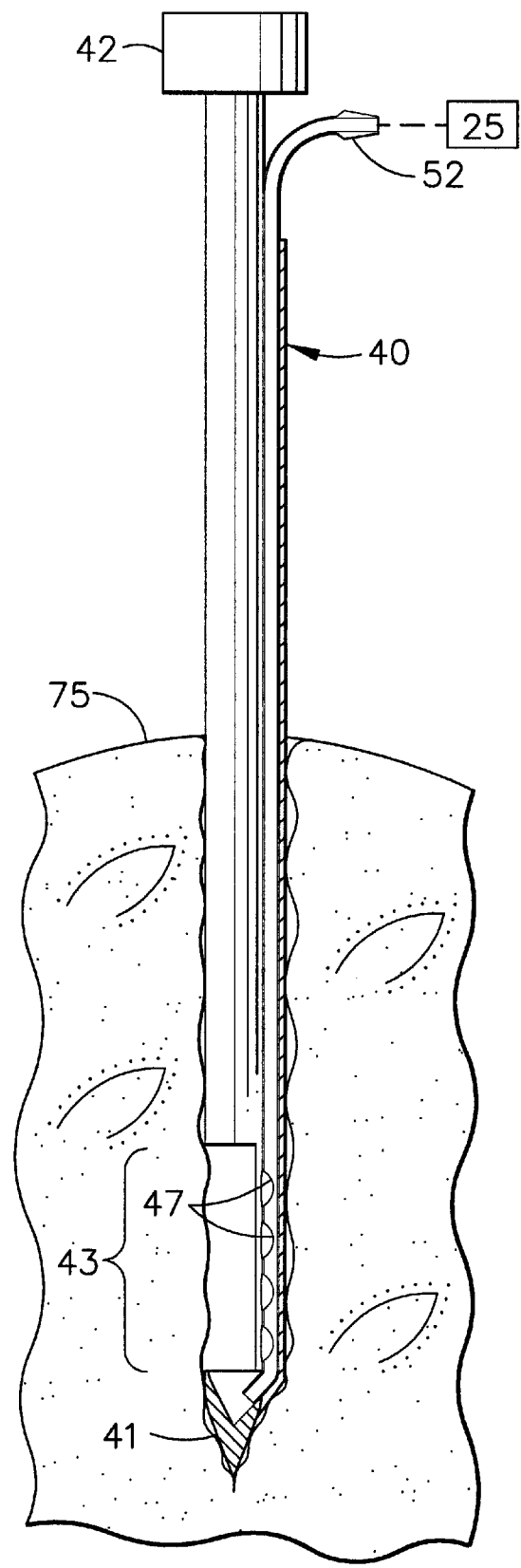
FIG. 14 is a cross-sectional side view of the surgical biopsy instrument of FIG. 12 with the cutting member removed.

FIG. 14 depicts the piercing needle 40 still embedded in the breast 25 after the cutting member 60 has been removed for further sampling. Cutting member 60 may be reinserted into passageway 44 of the piercing needle 40 if further sampling is necessary. Piercing needle 40 may be repositioned and the biopsy procedure can be repeated according to the steps detailed above until all of the sampling segments 64 have been used.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A method for acquiring at least one tissue sample from a body, said method comprising the steps of:

a) inserting a surgical biopsy instrument into said body, said surgical biopsy instrument having:

i) a piercing needle having a piercing tip and a tissue receiving port;

ii) a cutting member having a distal sampling segment, said sampling segment having a cutting edge and a bore therein, said sampling segment being breakable from said cutting member;

a) acquiring a tissue sample within said sampling segment of said cutting member, said tissue sample taken at said tissue receiving port of said piercing needle;

b) removing the sampling segment containing the tissue sample from said piercing needle; and c) breaking said sampling segment containing the tissue sample from said cutting member.

2. The method according to claim 1, including providing a vacuum source and acquiring the tissue sample by drawing tissue from said body into said tissue receiving port with said vacuum source.

3. The method according to claim 1, including providing a cutting member formed from a plurality of sampling segments breakably attached to adjacent sampling segments of said cutting member, said cutting member having a distal-most sampling segment, and sampling a second tissue sample at said tissue sampling port with a distal-most sampling segment.

4. The method according to claim 3, further comprising removing the distal-most sampling segment and the second tissue sample from said instrument.

5. The method according to claim 4, further comprising breaking said distal-most sampling segment with the second tissue sample from said cutting member.

6. The method according to claim 3, including providing an identifier on each of said plurality of sampling segments.

7. The method according to claim 6, including providing a number as an identifier on each of said plurality of sampling segments.

8. The method according to claim 3, including providing an external frangible layer on said cutting member to breakably hold together said plurality of sampling segments.

9. The method according to claim 8, including providing perforations in said external frangible layer to reduce the force to break each of said plurality of sampling segments from said cutting member.

* * * * *